(12) United States Patent
Hayes et al.

(10) Patent No.: US 9,243,877 B2
(45) Date of Patent: Jan. 26, 2016

(54) DETONATOR IGNITION PROTECTION AND DETECTION CIRCUIT

(75) Inventors: Michael J. Hayes, Collinsville, CT (US); Laura B. Hayes, legal representative, Collinsville, CT (US); Thomas A. Hoopes, Sandy, UT (US); Mark I. Jurras, Canton, CT (US)

(73) Assignee: DYNO NOBEL INC., Salt Lake City, UT (US)

( * ) Notice: Subject to any disclaimer, the term of this patent is extended or adjusted under 35 U.S.C. 154(b) by 314 days.

(21) Appl. No.: 13/994,405

(22) PCT Filed: Dec. 19, 2011
(Under 37 CFR 1.47)

(86) PCT No.: PCT/US2011/065722
§ 371 (c)(1),
(2), (4) Date: Sep. 25, 2013

(87) PCT Pub. No.: WO2012/087866
PCT Pub. Date: Jun. 28, 2012

(65) Prior Publication Data
US 2015/0233690 A1 Aug. 20, 2015

Related U.S. Application Data

(60) Provisional application No. 61/424,759, filed on Dec. 20, 2010.

(51) Int. Cl.
*F42B 3/188* (2006.01)
*F42C 15/40* (2006.01)
(Continued)

(52) U.S. Cl.
CPC ............... *F42C 15/40* (2013.01); *F42C 11/001* (2013.01); *G01R 25/00* (2013.01); *G01R 31/2832* (2013.01); *H01T 13/58* (2013.01); *F42B 3/188* (2013.01)

(58) Field of Classification Search
CPC ............ F42B 3/18; F42B 3/185; F42B 3/188; F42D 1/05; G01R 25/00

USPC ........... 102/202, 202.1, 202.5, 202.7, 202.11, 102/202.12, 206, 202.9
See application file for complete search history.

(56) References Cited

U.S. PATENT DOCUMENTS 3,022,446 A 2/1962 Irish, Jr.
3,343,491 A * 9/1967 Peters, Jr. ................ F42C 11/00
102/202.2

(Continued)

FOREIGN PATENT DOCUMENTS

CN 101241146 A 8/2008
DE 3443967 A1 6/1986

(Continued)

OTHER PUBLICATIONS

"A Microprocessor-Baded Intelligent Multi-Function Test Instrument"; Author: Dr. D.P. Mital; Elecktor Electronics; vol. 14, No. 161; XP000120422; ISSN: 0268-4519; Nov. 1988; 5 pgs.

(Continued)

*Primary Examiner* — Samir Abdosh
*Assistant Examiner* — John D Cooper
(74) *Attorney, Agent, or Firm* — Cantor Colburn LLP (57) ABSTRACT

An ignition circuit (200) includes: an igniter (210) having first (211) and second (212) terminals; a first diode (225) electrically connected in series with the igniter at the first terminal; a second diode (230) electrically connected in series with the igniter at the second terminal. The first and second diodes each have an anode terminal (226, 231) and a cathode terminal (227, 232), wherein like terminals of the first and second diodes are electrically connected to the igniter, thereby defining proximal terminals and distal terminals. A capacitor (235) is electrically connected across the distal terminals and connectable in parallel with a series-connected energy source (215) and switch (220). The energy source and a switch are electrically connectable across the distal terminals via test lead wires. Current flow through the igniter sufficient to ignite the igniter is prevented until an ignition voltage is applied to the distal terminals that is equal to or greater than the reverse breakdown voltage of the first diode or the second diode.

19 Claims, 5 Drawing Sheets

(51) Int. Cl.
*F42C 11/00* (2006.01)
*H01T 13/58* (2011.01)
*G01R 31/28* (2006.01)
*G01R 25/00* (2006.01)

(56) References Cited

U.S. PATENT DOCUMENTS

| | | | | |
|---|---|---|---|---|
| 6,470,803 | B1* | 10/2002 | Liu | F42D 1/05 102/206 |
| 6,512,383 | B1* | 1/2003 | Gomory | G01R 27/16 324/543 |
| 2004/0066833 | A1* | 4/2004 | Blakeley, III | G01J 5/041 374/120 |
| 2004/0239308 | A1* | 12/2004 | Fazzina | G01R 15/125 324/99 D |
| 2008/0223241 | A1* | 9/2008 | Hurley | F42B 3/18 102/202.4 |
| 2009/0283004 | A1* | 11/2009 | Teowee | F42D 1/05 102/215 |
| 2012/0079956 | A1* | 4/2012 | Jurras, III | F42B 3/18 102/202.7 |

FOREIGN PATENT DOCUMENTS

| | | |
|---|---|---|
| EP | 1544570 A1 | 6/2005 |
| JP | 05060797 A | 3/1993 |
| WO | 2008112234 A1 | 9/2008 |

OTHER PUBLICATIONS

PCT International Search Report for International Application No. PCT/US2011/065722; International Filing Date: Dec. 19, 2011; Date of Mailing: Mar. 26, 2012; 6 pgs.

PCT Written Opinion for International Application No. PCT/US2011/065722; International Filing Date: Dec. 19, 2011; Date of Mailing: Apr. 2, 2013; 10 pgs.

* cited by examiner

DETONATOR IGNITION PROTECTION AND DETECTION CIRCUIT

BACKGROUND OF THE INVENTION

The present invention relates to electric and electronic detonators and, more specifically, to such detonators being protected against inadvertent firing by stray or induced electrical currents, magnetic fields and the like, and even more specifically, to such detonators having a means for testing the electrical integrity of associated downhole test lead wires disposed in a conductive and/or galvanic environment.

U.S. Pat. No. 5,179,248 (the '248 patent), issued Jan. 12, 1993 to J. Keith Hartman et al. and entitled "Zener Diode For Protection Of Semiconductor Explosive Bridge", discloses protection of a semiconductor bridge against inadvertent firing by connecting a zener diode across the conductive metal lands forming part of the semiconductor bridge. As explained at column 3, line 14 et seq., a semiconductor bridge device includes a pair of spaced-apart metal lands disposed in ohmic contact on a doped semiconductor layer with a gap between the lands. In response to a voltage or current equal to or in excess of a predetermined level and duration being applied to the gap between the lands, a plasma is formed in the gap with sufficient energy to initiate an explosive disposed in the gap. The device for preventing accidental discharge includes and preferably consists of a zener diode having anode and cathode electrodes respectively connected to the first and second lands of the semiconductor bridge device.

U.S. Pat. No. 5,309,841 (the '841 patent), issued May 10, 1994 to J. Keith Hartman et al. and entitled "Zener Diode For Protection of Integrated Circuit Explosive Bridge", expands on the disclosure of the '248 Patent, including disclosure of circuits adding an energy storage capacitor and energy source in parallel with the zener diode and incorporating the elements into an integrated circuit.

As disclosed in both the '248 patent (col. 6, line 56 through col. 7, line 7; FIG. 3) and the '841 patent (col. 7, lines 20-39; FIG. 3), protection against premature firing of the semi-conductor explosive bridge is accomplished via waveform clipping by the protective zener diode.

Commonly assigned U.S. Patent Publication 2008/0223241A1, published Sep. 18, 2008, to Eldon K. Hurley and entitled "Detonator Ignition Protection Circuit", discloses a resistor disposed as part of the protection circuit to provide an electrical path in front of protection diodes for pre-testing the integrity of electrical connections from the firing station up to the protection circuit and igniter, and for protecting the igniter against stray static voltages.

While existing protective schemes for detonator devices may be suitable for their intended purpose, there remains, however, a need in the art for improved protective schemes that provide improved protection against possible stray voltage conditions that could cause unplanned initiation of a detonator, and a need in the art for improved circuit testing schemes that provide improved circuit testing under conditions where the test lead wires are disposed in conductive and/or galvanic environments.

SUMMARY OF THE INVENTION

An embodiment of the invention includes an ignition circuit for a detonator connectable downstream of test lead wires, the test lead wires being connectable to an energy source and switch, which are electrically connected in series with each other upstream of the test lead wires. The ignition circuit includes: an igniter having a first terminal and an opposing second terminal; a first diode electrically connected in series with the igniter at the first terminal; a second diode electrically connected in series with the igniter at the second terminal; the first and second diodes each having an anode terminal and a cathode terminal, wherein like terminals of the first and second diodes are electrically connected to the igniter, thereby defining proximal terminals proximate the igniter and distal terminals on an opposing side of each respective diode; and, a capacitor electrically connected across the distal terminals and connectable in parallel with the series-connected energy source and switch. The energy source and a switch electrically connected in series with each other are electrically connectable across the distal terminals via the test lead wires. The first and second diodes are electrically connected to the igniter in such a manner that results in a current flow through the igniter in response to a current flow through the first and second diodes for all voltage conditions at the distal terminals that produces a current flow through the first and second diodes, the current flow through the igniter being the same as the current flow through the first and second diodes. Current flow through the igniter sufficient to ignite the igniter is prevented until an ignition voltage is applied to the distal terminals that is equal to or greater than the reverse breakdown voltage of the first diode or the second diode.

An embodiment of the invention includes a method for testing an ignition circuit of a detonator having two test lead wires, the ignition circuit having a predefined capacitance and a predefined resistance range as measured at an upstream end of the two test lead wires connected to the detonator. The method, using an electrical circuit tester, includes: measuring a DC resistance of the ignition circuit from a reference point upstream of and across the two test lead wires; comparing the measured resistance with the predefined resistance range, and adjusting a circuit gain where the measured resistance is within the predefined resistance range, but on a low side of the range; injecting an AC reference voltage into the two test lead wires, and calculating a resultant phase angle between the AC reference voltage and a resultant AC current; determining if the calculated phase angle is within a predefined range based on the predefined capacitance; and, providing a signal in response to at least one of: the measured resistance being outside of the predefined resistance range; the calculated phase angle being outside of the predefined range; the measured resistance being inside the predefined resistance range; and, the calculated phase angle being inside the predefined range.

An embodiment of the invention includes an electrical circuit tester for practicing the aforementioned method. The electrical circuit tester includes: a housing having input/output ports disposed and configured for electrical communication external of the housing; a controller disposed within the housing; a user interface disposed and configured in electrical communication with the controller; and DC and AC circuitry disposed and configured in electrical communication with the controller. The DC circuitry is configured to provide a DC voltage at the input/output ports, and to receive a DC current signal in response to the input/output ports being electrically connected to an electrical impedance, wherein the controller is responsive to executable instructions to calculate a DC resistance based on the DC voltage and the DC current signal. The AC circuitry is configured to provide an AC reference voltage waveform at the input/output ports, and to receive an AC current waveform in response to the input/output ports being electrically connected to the electrical impedance, wherein the controller is responsive to executable instructions to calculate an electrical phase angle between the AC reference voltage waveform and the AC current waveform.

BRIEF DESCRIPTION OF THE DRAWINGS

Referring now to the drawings, which are meant to be exemplary and not limiting, and wherein like elements are numbered alike in the accompanying Figures.

DETAILED DESCRIPTION OF THE INVENTION

An embodiment of the invention, as shown and described by the various figures and accompanying text, provides a protection and testing scheme for preventing unplanned initiation of a detonator that may be used for seismic exploration, oil/gas well stimulation, or blasting in hazardous environments, while providing sufficient ignition voltage to an igniter upon command without substantially increasing the amount of energy that an energy source must be capable of delivering to the detonator for delayed ignition, and for testing the electrical integrity of the downhole test lead wires connected to the ignition circuit, where the test lead wires may be partially or completely abraded and the downhole environment may be conductive and/or galvanic in nature.

Figure 1:
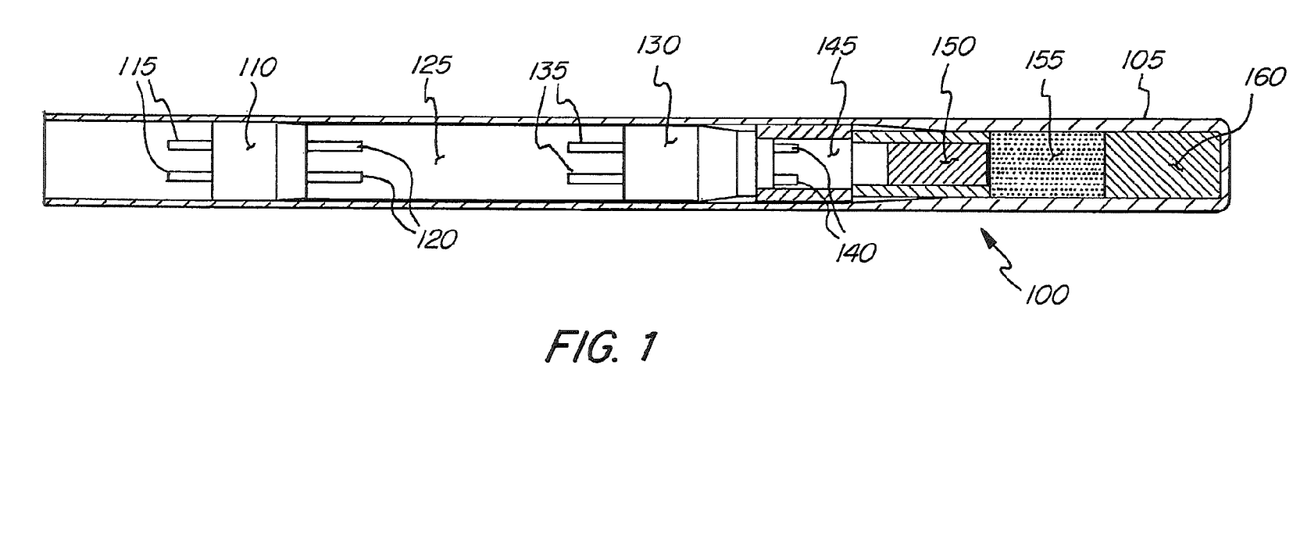
FIG. 1 depicts in cross-sectional schematic view a detonator shell for use in accordance with an embodiment of the invention.

Referring to FIG. 1, an exemplary detonator 100 is depicted in cross-sectional schematic view having a detonator shell 105 that houses an input connector 110 having input pins 115 and output pins 120, a protection circuit 125 (to be discussed in more detail below with reference to FIG. 2), an output connector 130 having input pins 135 and output pins 140, an ignition region 145, a first stage detonator charge 150, a second stage detonator charge 155, and a third stage detonator charge 160. Receipt of a planned ignition voltage at input pins 115 is transferred to protection circuit 125 via output pins 120, which properly passes through protection circuit 125 in a manner to be discussed in more detail below to cause a chain reaction starting with ignition of an igniter 210 (discussed below with reference to FIG. 2) disposed within ignition region 145, which in succession causes firing of the first stage detonator charge 150, the second stage detonator charge 155, and then the third stage detonator charge 160. In an embodiment, the detonator shell 105 is standard commercial detonator shell having a 0.25 inch (6.5 mm) nominal diameter opening, the first stage detonator charge 150 is diazo (diazo dinitro phenol, usually referred to as DDNP), the second stage detonator charge 155 is loose PETN (pentaerythritol tetranitrate, also known as penthrite), and the third stage detonator charge 160 is pressed PETN.

Figure 2:
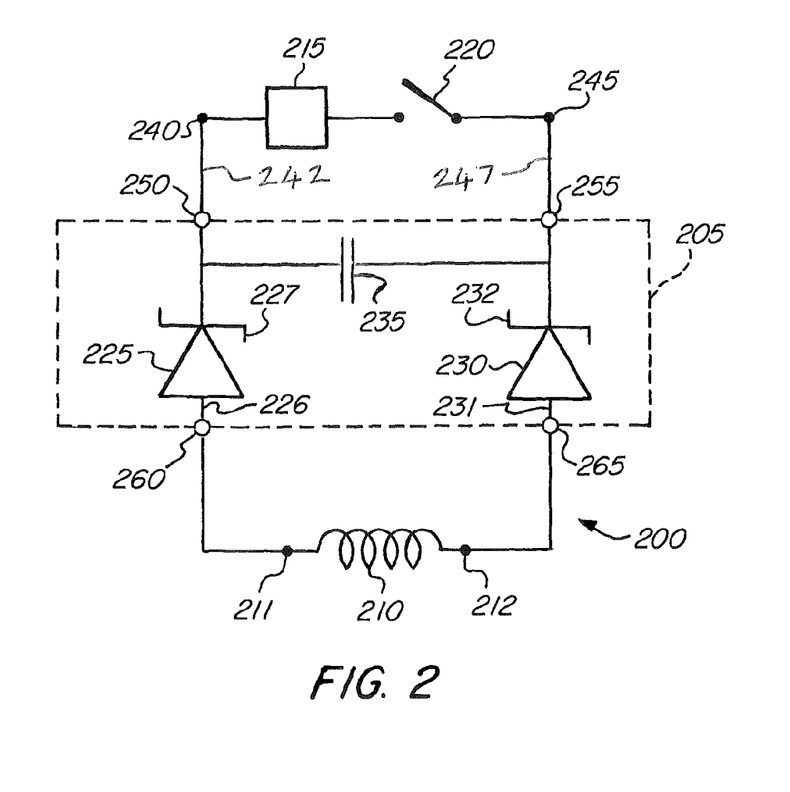
FIG. 2 depicts a schematic of an exemplary firing circuit in accordance with an embodiment of the invention.

Referring now to FIG. 2, an exemplary ignition circuit 200 is depicted having a protection/detection circuit 205, an igniter 210 having first 211 and second 212 terminals, a source of electrical energy 215, and a switch 220. In an embodiment, protection/detection circuit 205 includes a first diode 225 having anode 226 and cathode 227, a second diode 230 having anode 231 and cathode 232, and a capacitor 235. As illustrated, first diode 225 is electrically connected in series with igniter 210 at first terminal 211, and second diode 230 is electrically connected in series with igniter 210 at the opposing second terminal 212, wherein like terminals (anodes 226 and 231 for example) of the first and second diodes 225, 230 are electrically connected to the igniter 210, thereby defining proximal terminals proximate the igniter and distal terminals on an opposing side of each respective diode. As also illustrated, energy source 215 and switch 220 are electrically connected in series with each other, and electrically connected across the distal terminals of first and second diodes 225, 230.

In relating FIG. 2 to FIG. 1, contact points 240, 245 in FIG. 2 are electrically synonymous with input pins 115 in FIG. 1, contact points 250, 255 in FIG. 2 are electrically synonymous with output pins 120 in FIG. 1, contact points 260, 265 in FIG. 2 are electrically synonymous with input pins 135 in FIG. 1, and terminals 211, 212 in FIG. 2 are electrically synonymous with output pins 140 in FIG. 1. While not specifically depicted in FIG. 1, it will be appreciated by the description and illustration disclosed herein that the energy source 215 and switch 220 illustrated in FIG. 2 are connected to pins 115 of detonator 100 in FIG. 1 (synonymous with contact points 240, 245 of FIG. 2), thereby providing the necessary energy, switching means and ignition voltage to fire igniter 210 disposed in ignition region 145. In an embodiment, energy source 215 is a battery, a charged capacitor, or any other energy source suitable for the purposes disclosed herein, and switch 220 is an electronic switching device, or any other switching device suitable for the purposes disclosed herein, where switch 220 is a separate component or integrated within a time delay module. The electrical connection between contact points 240 and 250 is herein referred to as a test lead wire (leg wire) 242, and the electrical connection between contact point 245 and 255 is herein referred to as a test lead wire 247. Test lead wires 242, 247 are collectively herein referred to as a lead wire set, which extends from the downhole detonator 100 to the surface of the bore hole (downhole) in which the detonator 100 is placed.

As mentioned above, capacitor 235 is disposed in electrical connection across the distal terminals of diodes 225, 230, and in parallel with the series-connected energy source 215 and switch 220, but part of the protection/detection circuit 205. That is, capacitor 235 is specifically disposed in the test bore hole, downstream of the test lead wires 242, 247, and is part of the protection/detection circuit 205 of the detonator 100. When arranged as illustrated, capacitor 235 provides an electrical path in front of the diodes 225, 230 for pre-testing the integrity of electrical connections from the firing station (not illustrated but connectable to pins 115) up to the protection/detection circuit 205 and igniter 210, and for protecting the circuit 205 against stray AC voltages such as those induced by RF (radio frequency) energy. The electrical path provided by the parallel-connected capacitor 235 provides a downhole impedance having a reactance that is substantially capacitive in its electrical characteristic. As such, when an input reference AC voltage waveform, having a peak value below the ignition threshold voltage of igniter 210, is applied across the contact points 240, 245, the resultant AC current waveform conducting through the downhole impedance, that is, through the test lead wires 242, 247 and the capacitor 235, will have a phase shift of about 90-degrees relative to the input reference AC voltage waveform.

Compared to a simple resistance or continuity check across contact points 240, 245, checking for the presence of a phase shift angle associated with the downhole protection/detection circuit 205 provides for a higher level of confidence that the wires 242, 247 of the lead wire set are suitably in tact for their intended purpose. As previously discussed, the term lead wire set refers to those wires 242, 247 that are part of the circuit 200 in FIG. 2 between points 240 and 250, and between points 245 and 255, which are the wires that drop down a bore hole (downhole) in which the detonator 100 is placed.

In a conductive downhole environment, such as in the presence of high saline soil content and an abraded lead wire set, or in a galvanic downhole environment, such as in the presence of dissimilar metals and an abraded lead wire set in an acidic environment, testing for continuity or resistance across the lead wires 242, 247 may not provide valid test results, as the lead wire set may be partially or completely shorted out with respect to each other, thereby suggesting that a no-fire condition may be present. On the other hand, testing for the presence of a phase shift angle between the input reference AC voltage and the resultant AC current, will produce a more valid test result as long as the wires 242, 247 of the lead wire set are not dead-shorted (that is, as long as there is not essentially zero resistance between the two lead wires). For example, even if there is some electrical communication between the two lead wires 242, 247, there may be sufficient impedance to carry a firing voltage to the igniter 210, which a continuity or resistance check across the lead wires 242, 247 will not recognize, but a phase-shift check will.

Accordingly, in an embodiment employing a parallel-connected capacitor 235 as illustrated in FIG. 2, a circuit integrity check may be accomplished by performing both a resistance check and a phase shift check, which will now be described in connection with FIG. 4.

Figure 4:
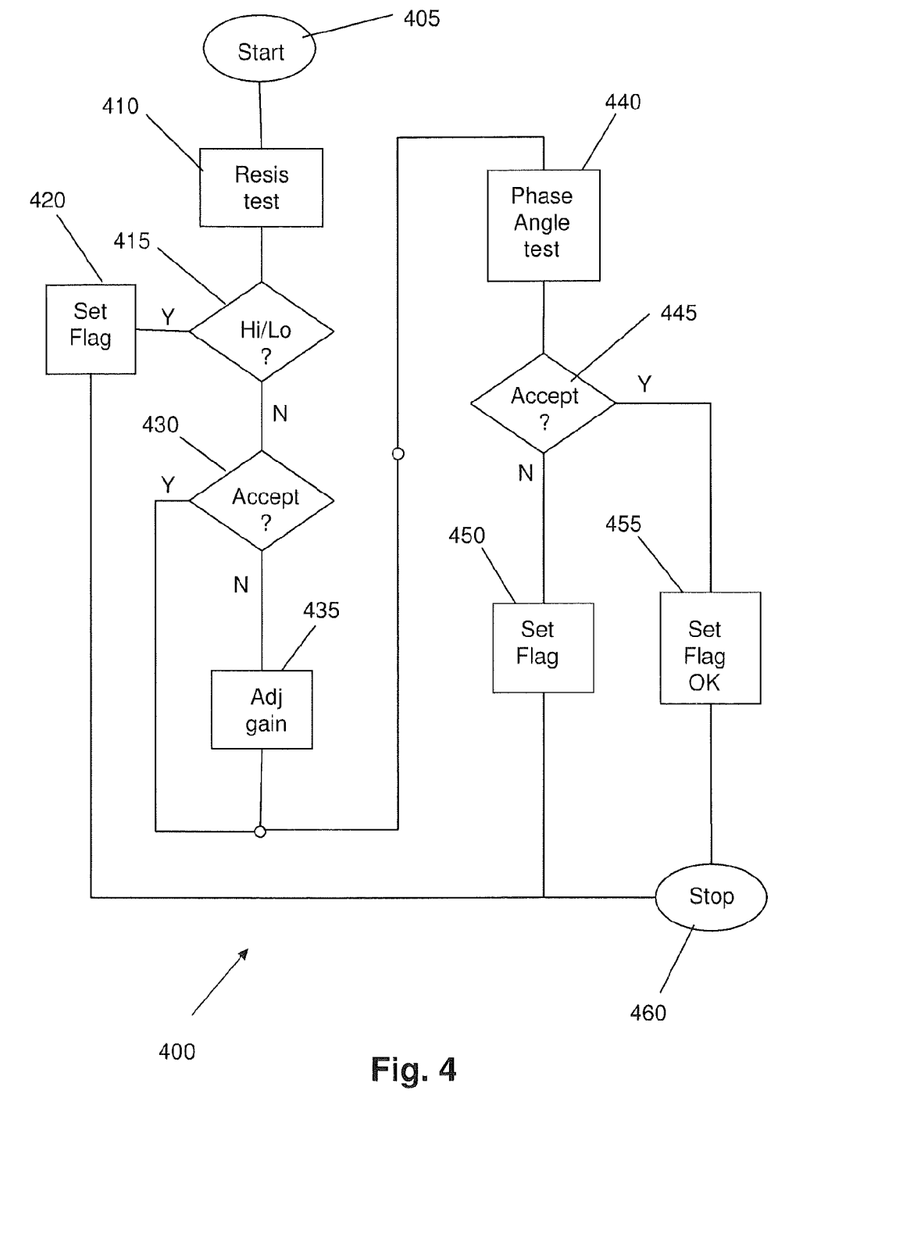
FIG. 4 depicts a flowchart of a method for testing the firing circuit of FIG. 2 in accordance with an embodiment of the invention.

FIG. 4 depicts in flowchart form a method 400 of using an electrical circuit tester (discussed below in connection with FIG. 5) for checking the integrity of the downhole protection/detection circuit 205, which starts at block 405. At block 410, a DC voltage signal is injected into the test lead wires 242, 247 by the circuit tester, and the resistance of the downhole protection/detection circuit 205 and connected test lead wires 242, 247 is checked against a known resistance range, which takes into account contact resistance, lead wire resistance (varies based on length), and stray lead-to-lead current-leakage paths. As would be appreciated by one skilled in the art, the resistance of each detonator and test lead wire set is pre-tested and logged prior to inserting the combination into a downhole, thereby providing sufficient information to unambiguously define the known resistance range. Checking for the DC resistance provides information that is later used to determine whether to adjust a circuit gain of the circuit tester or not, where adjustment of the circuit gain allows for detection by the circuit tester of a phase angle shift when the DC resistance measurement is inside the known resistance range, but on the low side, which will be explained in more detail below.

At block 415, if the DC resistance of circuit 205 and test lead wires 242, 247 is too low or too high, more specifically outside of the known resistance range, process logic passes to block 420 where the circuit tester provides an indication (set flag) that the test lead wires are either shorted out, or substantially shorted out, or are open circuited, to the point where they will not be able to deliver an ignition voltage to the igniter 210 when such an ignition voltage is applied across the contact points 240, 245.

At block 430, the circuit tester determines if the DC resistance is within the known resistance range, and if so, if the DC resistance is on the low side of the known resistance range, which would be indicative of some leakage between the test lead wires, but not enough to prevent ignition of igniter 210 on command. If the DC resistance is within the known resistance range, but on the low side of the range, process logic passes to block 435 where a circuit gain of the circuit tester is adjusted so that a phase angle measurement signal, to be discussed further below, can be read. Process logic then passes to block 440.

If the DC resistance is within the known resistance range and is within an acceptable window of that range, that is, the DC resistance is not on the low side of the range, then process logic passes directly from block 430 to block 440.

At block 440, an AC voltage signal is injected into the test lead wires 242, 247 by the circuit tester, and the phase angle of the resultant AC current is checked against the phase angle of the applied AC voltage, where the phase angle shift caused by the parallel-connected capacitor 235 of the downhole protection/detection circuit 205 is of a known value, or is at least within a predefined range tested earlier prior to insertion of the detonator into the downhole. In an embodiment, the presence or absence of a phase angle between the AC voltage and the resultant AC current is sufficient to determine whether acceptable circuit conditions exist for proper firing of the igniter 210. In an embodiment, detection of a phase angle difference of between 60-135 electrical degrees is sufficient for the purposes disclosed herein. In an embodiment, the parallel-connected capacitor 235 has a value of about 0.1 micro-Farad to produce an acceptable and recognizable phase angle shift.

At block 445, the circuit tester determines if the phase angle is within the predefined range. If the phase angle shift is outside of the predefined range, then process logic passes to block 450, where the circuit tester provides an indication (set flag) that the test lead wires are either shorted out, or substantially shorted out, or are open circuited, to the point where they will not be able to deliver an ignition voltage to the igniter 210 when such an ignition voltage is applied across the contact points 240, 245.

If the phase angle is acceptable, within the predefined range, then process logic passes to block 455, where the circuit tester provides an indication (set flag OK) that the test lead wires are in satisfactory condition to deliver an ignition voltage to the igniter 210 when such an ignition voltage is applied across the contact points 240, 245.

From blocks 420, 450 and 455, process logic passes to block 460, where testing of a given downhole protection/detection circuit 205 is stopped and the test results logged for subsequent uploading or downloading for shotpoint mapping and/or other diagnostic purposes.

The method 400 is repeated as necessary or desired for each downhole protection/detection circuit 205.

Figure 5:
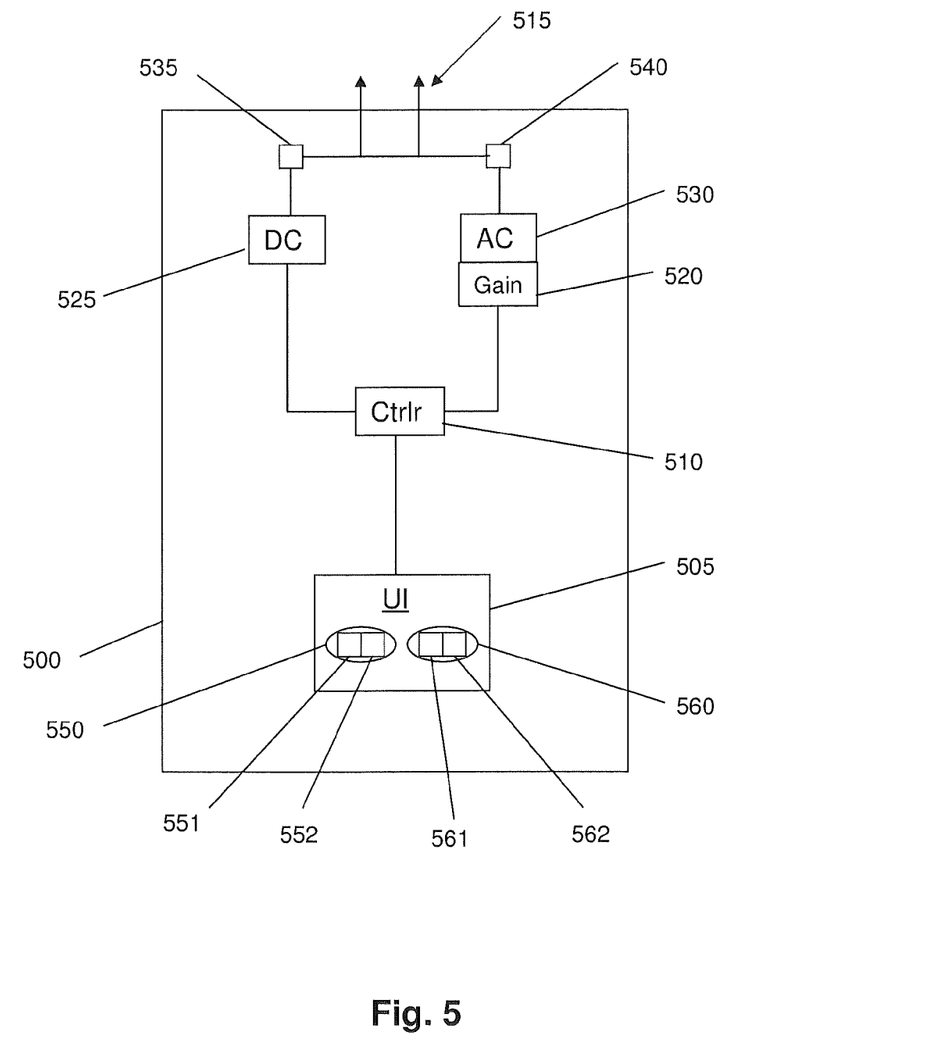
FIG. 5 depicts a block diagram schematic of an electrical tester for implementing the method of FIG. 4 in accordance with an embodiment of the invention.

FIG. 5 depicts in block diagram form an electrical circuit tester 500 suitable for practicing the method 400 of FIG. 4. A user interface 505, such as a keyboard, a keypad, a touchscreen, a display screen, light emitting diodes (LEDs), and/or any other input/output means suitable for the purposes disclosed herein, is in signal communication with a microprocessor-based controller 510, which is configured to control DC and AC voltage signal injection into test lead wires 242, 247, via DC and AC circuitry 525, 530, respectively, and to receive DC and AC test current signals, via DC and AC circuitry 525, 530, respectively, returned back to the circuit tester 500, via input/output ports 515. In an embodiment, electrical isolation between the DC and AC circuitry at the input/output ports 515 is provided by isolation circuitry 535, 540. Circuit tester 500 includes an adjustable gain circuit 520 controlled by controller 510 for amplifying the AC test current signal returned back to the circuit tester 500 in response to the controller 510 determining that the DC resistance of the protection/detection circuit 205 and connected test lead wires 242, 247 is within the known resistance range, but on the low side of the range. As discussed above in relation to block 435 of method 400, the adjustable gain circuit 520 of the circuit tester 500 is adjusted so that a phase angle measurement signal can be read, the phase angle being the phase shift in electrical degrees between the AC current and the AC voltage, which is determined by the controller 510. As will be appreciated by one skilled in the art, microprocessor-based controller 510 is responsive to executable instructions which when executed by the controller 510 is capable of implementing the aforementioned method 400.

As a result of circuit tester 500 implementing method 400, the user interface 505 provides a user with information relating to the electrical integrity of a downhole detonator 100, such as for example, whether the test leads 242, 247 are shorted-out or open-circuited, or whether the test leads 242, 247 have sufficient electrical integrity to support and deliver an ignition voltage to the igniter 210. As disclosed herein, the parallel-connected capacitor 235 provides a high level of confidence that the test results provided by the circuit tester 500 are accurate, even in conditions where the detonator 100 may have an abraded lead wire set in a downhole environment that is galvanic and/or has a high saline soil content.

In an embodiment, the output of the circuit tester 500 provides a first type of signal in response to the measured DC resistance being outside of the known resistance range, and provides a second type of signal in response to the calculated phase angle, or the adjusted phase angle if adjusted, being outside of the predefined phase angle range, both signals being indicative of a suspect lead wire set, which may or may not be functional for the same or a different reason. In an embodiment, the first type of signal is a red light displayed via a first optical lens 550, and the second type of signal is a red light displayed via a second optical lens 560. If the DC resistance is within the known resistance range, then green light is displayed at the first optical lens 550, and if the phase angle measurement is within the predefined phase angle range, then a green light is displayed at the second optical lens 560. In an embodiment, red and green LEDs (light emitting diodes) 551, 552, 561, 562, are disposed behind respective ones of the two lenses. Thus, if the LEDs of both optical lenses 550, 560 are green (red LEDs 551 and 561 are OFF, and green LEDs 552 and 562 are ON), then both the measured DC resistance and the measure phase angle are within the known and predefined ranges, indicating suitable lead wire conditions for firing the downhole detonator 100. Other signals may be combined with the two LED sets to provide additional information relating to the integrity of the downhole leadwire set. For example, high and low frequency sounds may be used to indicate high and low measurements, respectively, of the DC resistance and phase angle. Alternatively, the respective red LEDs may flash at high and low frequencies to indicate high and low measurements, respectively, of the DC resistance and phase angle. While embodiments of the invention are described employing LEDs as signal generators for presenting useful information to a user, it will be appreciated that other signal generators, such as indicia on a display screen for example, may be employed instead of or in combination with the LEDs. Such signal generators are contemplated and considered within the scope of the invention, and may be collectively referred to as first and second signal generators with reference to reference numerals 550, 560.

In accordance with an embodiment of the invention, current flow through igniter 210 sufficient to ignite igniter 210 is prevented until an ignition voltage is applied to the distal terminals (250, 255 for example) of diodes 225, 230 that is equal to or greater than the reverse breakdown voltage of the first diode 225 or the second diode 230.

In an embodiment, the first and second diodes 225, 230 are zener diodes having the same reverse breakdown voltage rating of 20 Volts, and are disposed such that their anodes 226, 231 are the proximal terminals (that is, anodes 226, 231 are electrically connected to igniter 210). In another embodiment, first and second diodes 225, 230 are zener diodes having the same reverse breakdown voltage rating of 200 Volts.

Figure 3:
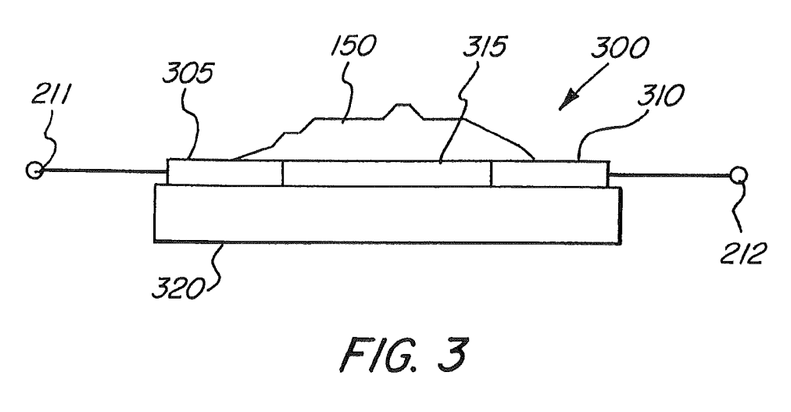
FIG. 3 depicts an alternate igniter to that depicted in FIG. 2 for use in accordance with an embodiment of the invention.

In an embodiment, igniter 210 is a bridgewire designed for contact with (for example, to be embedded within) an explosive device (for example, the first stage detonator charge 150) with a pair of lead wires extending from the bridgewire. However, it will be appreciated that other igniters suitable for the purposes disclosed herein may be employed in place of the bridgewire, such as a semiconductor bridge 300 for example, generally depicted in FIG. 3, having lands 305, 310 in electrical contact with a semiconductor layer 315, all disposed on a substrate 320, with the first stage detonator charge 150 being disposed across lands 305, 310 and semiconductor layer 315. Operation of such a semiconductor bridge 300 in the field of explosive detonators is well known in the art and is not discussed further herein.

In an embodiment, first diode 225, second diode 230, and capacitor 235 are all surface mounted on a circuit board, generally depicted by reference numeral 205 and the associated dashed-line graphical box depicted in FIG. 2. The combination of circuit board 205 with surface-mounted diodes 225, 230 and capacitor 235 (collectively referred to as surface-mounted components) is so dimensioned as to be insertable through the space defined by the opening of detonator shell 105, which in an embodiment is a standard commercial detonator shell having a 0.25 inch (6.5 mm) nominal diameter opening. When the circuit board with surface-mounted components is positioned within the detonator shell, the dielectric breakdown voltage between any of the surface-mounted components and the interior wall of the detonator shell is greater than the reverse breakdown voltage of each of the first diode 225 and the second diode 230.

Upon closure of the switch 220 (planned ignition), not only does the energy source 215 have sufficient energy to generate a voltage at the distal terminals 250, 255 in excess of the reverse breakdown voltage of the first diode 225 or the second diode 230 to generate sufficient current flow to ignite the igniter 210, but also the energy source 215 further has sufficient energy to permanently damage a reverse-biased one of the first and second diodes 225, 230. Since the detonator 100 is an intended self-destructive device, there is no need for either diode 225, 230 to be designed for passing a reverse-biased current without damage thereto. As such, diodes having a reverse-biased current rating far below the actual current passed are fully sufficient for the purposes disclosed herein, thereby permitting small diodes to be used in a compact design for the protection circuit 205.

In an embodiment and in the event of the switch 220 being closed, the energy source 215 has sufficient energy to generate an ignition voltage to ignite the igniter 210 that is equal to or greater than 1.1 times the reverse breakdown voltage of either of the first diode 225 and the second diode 230. And, in the event of the switch 220 being open, each of the first 225 and second 230 diodes have a reverse breakdown voltage sufficient to prevent the igniter 210 from firing upon the occurrence of a stray voltage at the distal terminals (250, 255 for example) less than the reverse breakdown voltage of the associated reverse-fed diode.

While embodiments of the invention have been described herein employing a circuit board 205 with diodes 225, 230 and capacitor 235 surface-mounted thereon, it will be appreciated that other packaging arrangements can be employed for the purposes disclosed herein, such as integrally molding diodes 225, 230 and capacitor 235 into a plug, again generally depicted by reference numeral 205 and the associated dashed-line graphical box depicted in FIG. 2, where the plug 205 with the integrally-molded diodes 225, 230 and capacitor 235 is so dimensioned as to be insertable through the space defined by the opening of a standard size 0.25 inch (6.5 mm) diameter detonator shell 105.

While embodiments of the invention have been described herein having anodes 226, 231 of first diode 225 and second diode 230, respectively, being connected to igniter 210, it will be appreciated that the scope of the invention also covers an arrangement where both diodes are reversed such that their cathodes 227, 232 are connected to igniter 210, as long as both diodes are oriented in the same direction such that no current will flow through igniter 210 if an unplanned voltage below the diode breakdown voltage is applied across the contact points 250, 255 of circuit 205.

Because diodes 225 and 230 are oriented in the same direction as illustrated in FIG. 2, that is, the diodes face each other in their forward directions, current flow is precluded by a voltage applied across the circuit at contact points 240, 245, until and unless the voltage exceeds the breakdown voltage of the diodes. Once the breakdown voltage is exceeded, current would then flow to energize the bridgewire.

If zener diodes are utilized as the diodes 240, 245, their breakdown voltage can be precisely specified and a specific all fire/no fire value can readily be established for the diode-protected detonator by utilizing methods and calculations well known to those skilled in the art. As discussed above, the facing diodes, for example, facing zener diodes, together with the other circuit components, can readily be positioned on a small board or molded into a plug, either of which will readily fit into the inside diameter, about 0.25 inches (6.5 mm), of a standard commercial detonator shell. The disclosed detonator is resistant to stray current engendered by radio frequency energy, static and any other electrical power that does not exceed the diode breakdown voltage.

It is contemplated that in an embodiment where first and second diodes 225, 230 are zener diodes each having a reverse breakdown voltage of 200 Volts, sufficient protection of igniter 210 will be provided against a standard 120 VAC-rms voltage at input pins 115 having a peak voltage of about 170 Volts. By employing zener diodes having a 200 Volt reverse breakdown voltage (first and second diodes 225, 230 in the contemplated embodiment) and a very small current rating (less than 2 milliamps for example), a massive energy pulse of 4-8 joules from a 400 Volt capacitor discharge firing system will result in a one-time use of diodes 225, 230, which will fail in conduction mode. Since diodes 225, 230 need to work only once, such an occurrence of failure in the conduction mode is perfectly acceptable for the purposes disclosed herein. An exemplary commercially available zener diode suitable for the purposes disclosed herein is part number 1SMB5956BT3G manufactured by Oakley Telecom, LC, having a nominal reverse zener voltage of 200 volts at a reverse current of 1.9 milliamps.

The accuracy of the timing of initiation of individual explosive charges in a multiple-charge blasting system must be closely controlled to achieve the desired fragmentation of ore and rock, and to reduce the influence of the blast on structures outside the blast zone. The accuracy of timing of the initiation of individual charges controls the effectiveness of the blast by providing the required distribution of blast induced shock-waves. Embodiments of the invention provide detonators that can be used for closely controlling the timing of the initiation of individual explosive charges in multiple-explosive charge blast operations. For example, for electronic delay of detonator 100, the test voltage provided to contact points 250, 255 of ignition circuit 200 could be safely raised to a level just below the breakdown voltage of diodes 225, 230 without concern of prematurely firing the very low energy igniter 210, thereby enabling better communication with other connected detonators within the multiple-charge blasting system. Additionally, and contrary to other blasting systems that employ a series-connected resistor to protect the igniter, which inherently results in an $I^2R$ power loss across the series-connected resistor during ignition, embodiments of the invention do not have such a power loss and therefore have more energy available from energy source 215 for use by electronic delay circuitry, communications, and controls of the blasting system. Further, through careful selection of the capacitor value the RF sensitivity of the detonator may be reduced by providing a shunt for RF energy coupled to the detonator through its leg wires.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. An ignition circuit configured for use with a detonator, the ignition circuit comprising:
    an energy source and a switch electrically connected in series with each other;
    test lead wires electrically connected to outside contact points of the series-connected energy source and switch;
    an igniter having a first terminal and an opposing second terminal;
    a first diode electrically connected in series with the igniter at the first terminal;
    a second diode electrically connected in series with the igniter at the second terminal;
    the first and second diodes each having an anode terminal and a cathode terminal, wherein like terminals of the first and second diodes are electrically connected to the igniter, thereby defining proximal terminals proximate the igniter and distal terminals on an opposing side of each respective diode;
    a capacitor electrically connected across the distal terminals and in parallel with the series-connected energy source and switch;

wherein the energy source and the switch are electrically connected across the distal terminals via the test lead wires;

the first and second diodes being electrically connected to the igniter in such a manner that results in a current flow through the igniter in response to a current flow through the first and second diodes for all voltage conditions at the distal terminals that produces a current flow through the first and second diodes, the current flow through the igniter being the same as the current flow through the first and second diodes;

wherein current flow through the igniter sufficient to ignite the igniter is prevented until an ignition voltage is applied to the distal terminals that is equal to or greater than the reverse breakdown voltage of the first diode or the second diode.

2. The ignition circuit of claim 1, wherein the first and second diodes have a same reverse breakdown voltage.

3. The ignition circuit of claim 2, wherein the first and second diodes are zener diodes.

4. The ignition circuit of claim 1, wherein the anode terminals of the first and second diodes are the proximal terminals.

5. The ignition circuit of claim 1, wherein the igniter comprises a bridgewire or a semi-conductor bridge.

6. The ignition circuit of claim 1, further comprising:
a circuit board having the first and second diodes surface mounted thereon;
wherein the circuit board with the surface-mounted diodes is so dimensioned as to be insertable through the space defined by the opening of a standard size one-quarter inch diameter detonator shell.

7. The ignition circuit of claim 6, wherein the dielectric breakdown voltage between the surface-mounted diodes and the interior wall of the detonator shell is greater than the reverse breakdown voltage of each of the first diode and the second diode.

8. The ignition circuit of claim 6, wherein the resistor is surface mounted on the circuit board.

9. The ignition circuit of claim 1, wherein upon closure of the switch the energy source has sufficient energy to generate a voltage at the distal terminals in excess of the reverse breakdown voltage of the first diode or the second diode, and to generate sufficient current flow to ignite the igniter.

10. The ignition circuit of claim 9, wherein upon closure of the switch the energy source further has sufficient energy to permanently damage a reverse-biased one of the first and second diodes.

11. The ignition circuit of claim 9, where in the event of the switch being closed the energy source further has sufficient energy to generate an ignition voltage to ignite the igniter that is equal to or greater than 1.1 times the reverse breakdown voltage of either of the first diode and the second diode.

12. The ignition circuit of claim 11, where in the event of the switch being open each of the first and second diodes have a reverse breakdown voltage sufficient to prevent the igniter from firing upon the occurrence of a stray voltage at the distal terminals equal to or less than the reverse breakdown voltage of the associated reverse-fed diode.

13. The ignition circuit of claim 1, further comprising:
a plug having the first and second diodes integrally molded therein;
wherein the plug with the integrally-molded diodes is so dimensioned as to be insertable through the space defined by the opening of a standard size one-quarter inch diameter detonator shell.

14. The ignition circuit of claim 1, wherein each of the first diode and the second diode have a reverse breakdown voltage of 200 volts.

15. A method for testing an ignition circuit of a detonator having two test lead wires, the ignition circuit having a predefined capacitance and a predefined resistance range as measured at an upstream end of the two test lead wires connected to the detonator, the method comprising:
using an electrical circuit tester:
measuring a DC resistance of the ignition circuit from a reference point upstream of and across the two test lead wires;
comparing the measured resistance with the predefined resistance range, and adjusting a circuit gain where the measured resistance is within the predefined resistance range, but on a low side of the range;
injecting an AC reference voltage into the two test lead wires, and calculating a resultant phase angle between the AC reference voltage and a resultant AC current;
determining if the calculated phase angle is within a predefined range based on the predefined capacitance;
providing a signal in response to at least one of: the measured resistance being outside of the predefined resistance range; the calculated phase angle being outside of the predefined range; the measured resistance being inside the predefined resistance range; and, the calculated phase angle being inside the predefined range.

16. The method of claim 15, wherein the providing a signal comprises:
providing a red light signal in response to the measured resistance being outside of the predefined resistance range and/or the calculated phase angle being outside of the predefined range; and
providing a green light signal in response to the measured resistance being inside of the predefined resistance range and/or the calculated phase angle being inside of the predefined range.

17. An electrical circuit tester comprising:
a housing having input/output ports disposed and configured for electrical communication external of the housing;
a microprocessor-based controller disposed within the housing;
a user interface disposed and configured in electrical communication with the controller; and
DC and AC circuitry disposed and configured in electrical communication with the controller;
wherein the DC circuitry is configured to provide a DC voltage at the input/output ports, and to receive a DC current signal in response to the input/output ports being electrically connected to an electrical impedance, wherein the controller is responsive to executable instructions to calculate a DC resistance based on the DC voltage and the DC current signal;
wherein the AC circuitry is configured to provide an AC reference voltage waveform at the input/output ports, and to receive an AC current waveform in response to the input/output ports being electrically connected to the electrical impedance, wherein the controller is responsive to executable instructions to calculate an electrical phase angle between the AC reference voltage waveform and the AC current waveform;
wherein the microprocessor-based controller is further responsive to executable instructions which when executed by the microprocessor-based controller is capable of performing a method, the method comprising:

measuring a DC resistance of the ignition circuit from a reference point upstream of and across the two test lead wires;

comparing the measured resistance with the predefined resistance range, and adjusting a circuit gain where the measured resistance is within the predefined resistance range, but on a low side of the range;

injecting an AC reference voltage into the two test lead wires, and calculating a resultant phase angle between the AC reference voltage and a resultant AC current;

determining if the calculated phase angle is within a predefined range based on the predefined capacitance;

providing a signal in response to at least one of: the measured resistance being outside of the predefined resistance range; the calculated phase angle being outside of the predefined range; the measured resistance being inside the predefined resistance range; and, the calculated phase angle being inside the predefined range.

18. The electrical circuit tester of claim 17, further comprising:
an adjustable gain circuit disposed in signal communication with the controller and configured to amplify the AC current waveform in response to the controller determining that the calculated DC resistance is within a known resistance range, but on a low side of the range.

19. The electrical circuit tester of claim 18, wherein:
the user interface comprises a first signal generator and a second signal generator, the first signal generator being responsive to a value of the calculated DC resistance, and the second signal generator being responsive to a value of the calculated electrical phase angle.

* * * * *